(12) United States Patent
Hirai

(10) Patent No.: US 7,751,741 B2
(45) Date of Patent: Jul. 6, 2010

(54) OPTICAL SENSOR AND IMAGE FORMING APPARATUS INCLUDING SAME

(75) Inventor: Shuji Hirai, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 111 days.

(21) Appl. No.: 12/120,702

(22) Filed: May 15, 2008

(65) Prior Publication Data
US 2008/0292360 A1    Nov. 27, 2008

(30) Foreign Application Priority Data
May 21, 2007    (JP) .............................. 2007-133899

(51) Int. Cl.
*G03G 15/00*    (2006.01)
*G03G 21/00*    (2006.01)

(52) U.S. Cl. .......................................... 399/74; 399/98

(58) Field of Classification Search .................. 399/74, 399/64, 49, 98, 99; 356/445
See application file for complete search history.

(56) References Cited

U.S. PATENT DOCUMENTS

| | | | |
|---|---|---|---|
| 6,757,512 | B2 | 6/2004 | Miyawaki et al. |
| 6,975,338 | B2 | 12/2005 | Hirai et al. |
| 7,110,917 | B2 | 9/2006 | Matsuura et al. |
| 7,151,901 | B2 | 12/2006 | Hirai |
| 7,203,431 | B2 | 4/2007 | Shoji et al. |
| 7,327,962 | B2 | 2/2008 | Shoji et al. |
| 2005/0002054 | A1 | 1/2005 | Shoji et al. |
| 2005/0281596 | A1 | 12/2005 | Nakagawa et al. |
| 2006/0182451 | A1 | 8/2006 | Shoji et al. |
| 2007/0258723 | A1 | 11/2007 | Nakazato et al. |
| 2008/0075476 | A1 | 3/2008 | Nakazato et al. |
| 2008/0145089 | A1* | 6/2008 | Takahashi .................... 399/74 |
| 2008/0253793 | A1 | 10/2008 | Ishibashi et al. |

FOREIGN PATENT DOCUMENTS

| | | |
|---|---|---|
| JP | 2-111162 (U) | 9/1990 |
| JP | 2002-268314 | 9/2002 |
| JP | 2003-261356 | 9/2003 |

(Continued)

OTHER PUBLICATIONS

Machine translation of JP 2002-268314 A dated Oct. 26, 2009.*

*Primary Examiner*—Sophia S Chen
(74) *Attorney, Agent, or Firm*—Oblon, Spivak, McClelland, Maier & Neustadt, L.L.P.

(57) ABSTRACT

An optical sensor includes a light-emitting element for directing light to an image, a light-receiving element for receiving light reflected by the image, a normal detection optical path for allowing the light emitted by the light-emitting element and the light reflected from the image to follow a normal detection optical path during normal operation, a calibration reflecting plate disposed inside the optical sensor for reflecting light from the light-emitting element when sensitivity is calibrated, a calibration optical path for allowing the light emitted by the light-emitting element to follow a calibration optical path to the light-receiving element when the emitted light is reflected by the calibration reflecting plate, and a first optical function element disposed in the calibration optical path and switchable between a light permeating state, in which the light passes therethrough, and a light intercepting state, in which the light is blocked, when voltage is applied.

11 Claims, 6 Drawing Sheets

FOREIGN PATENT DOCUMENTS

| | | |
|---|---|---|
| JP | 2003-335553 | 11/2003 |
| JP | 2004-139134 | 5/2004 |
| JP | 3661446 | 4/2005 |
| JP | 2005-257430 A * | 9/2005 |
| JP | 2005-274630 | 10/2005 |

* cited by examiner

REFLECTED LIGHT — EMITTED LIGHT

FIG. 10

OPTICAL SENSOR AND IMAGE FORMING APPARATUS INCLUDING SAME

CROSS-REFERENCE TO RELATED APPLICATIONS

This patent application is based on and claims priority pursuant to 35 U.S.C. §119 from Japanese Patent Application No. 2007-133899 filed on May 21, 2007 in the Japan Patent Office, the entire contents of which is hereby incorporated herein by reference.

BACKGROUND OF THE INVENTION

1. Field of the Invention

Exemplary aspects of the present invention generally relate to an optical sensor and an electrophotographic image forming apparatus using the same, and more particularly, to an optical sensor for detecting image information and an electrophotographic image forming apparatus, such as a copier, a printer, a facsimile, and a multi-function machine, using the same.

2. Description of the Background Art

Various types of optical sensors for detecting image information used in an electrophotographic image forming apparatus using dry toner, and technologies relating to the image forming apparatus equipped with such an optical sensor, have been proposed.

A typical example of a related-art optical sensor is that disclosed in Unexamined Utility Model Application Publication Hei 02-111162, which proposes a shutter device for an optical detection element that is included in a toner density control unit that regulates the toner density of a developing unit by enabling the optical detection element to detect light reflected from a visible image formed on a photoreceptor. The shutter device includes a shutter member that is disposed between the optical detection element and the photoreceptor and protects a surface of the optical detection element from contamination. The shutter member includes a window reciprocally movable in predetermined directions so that a light emitting area and a light receiving area of the optical detection element can be opened and closed. The shutter device includes a calibration plate disposed on a rear surface of the shutter member facing the light emitting area and the light receiving area, when the window is at a closed position.

One example of the optical sensor utilized in an image forming apparatus that uses electrophotography to form an image, and which requires calibration of its sensitivity (hereinafter "sensitivity calibration" or simply "calibration"), is a toner adhesion sensor for measuring an amount of toner adhesion. Such an optical sensor is normally an analogue sensor that measures the amount of toner adhesion on the basis of a voltage value. Calibration is needed because the amount of light of the light emitting element (for example, LED) may fluctuate over time due to deterioration of the, causing an analogue output value to fluctuate.

The toner adhesion sensor measures the amount of toner adhesion by irradiating a toner image formed on a toner image bearing member such as a photoreceptor and an intermediate transfer belt with light and detecting the amount of the reflected light.

There are two types of known methods for measuring an amount of toner adhesion. One method uses specular light, that is, specularly reflected light, and another method uses diffusely reflected light. The specular light is used to measure mainly an amount of black toner adhesion. The diffusely reflected light is used to measure mainly an amount of color toner adhesion.

The detection principle of the method using the specular light involves detecting a state of the specular light specularly reflected from the surface of the toner image bearing member through the toner image formed on the toner image bearing member. As a result, however, the intensity of the specular light is weakened.

The detection principle of the method using the diffusely reflected light involves detecting an intensity of the diffusely reflected light reflected by the toner image itself formed on the toner image bearing member.

When there is no toner image on the toner image bearing member, an output value of the sensor using the specular light is at its greatest, whereas the output value of the sensor using the diffusely reflected light is approximately zero. Such a difference in the output value may determine the operation of the sensitivity calibration in the image forming apparatus.

Accordingly, when the surface of the toner image bearing member has a surface similar to the specular surface of the photoreceptor, for example, the sensor using the specular light can calibrate the sensitivity using the specular light specularly reflected by the surface of the toner image bearing surface. For example, when the sensor detects the surface of the toner image bearing surface, the light emission intensity of the light emitting element is adjusted such that the output value becomes, for example, 4V.

On the other hand, in the sensor using the diffusely reflected light, the output value may be approximately zero relative to the surface of the toner image bearing member, making calibration impossible. Calibration requires adjusting the intensity of light emission by the light emitting element such that a reference voltage is output when the sensor detects a reference surface. However, when an output voltage is almost zero, it is hardly possible to adjust the intensity of light emission of the light emitting element.

As described above, when the surface of the toner image bearing member is substantially similar to the specular surface as commonly implemented in the image forming apparatuses, the sensor using the diffusely reflected light cannot calibrate sensitivity using the surface of the toner image bearing member, and therefore requires a reflecting plate for calibration.

In a case in which the sensor detecting the specular light and the sensor detecting the diffusely reflected light are both provided in one sensor, the calibration result of the sensor detecting the specular light can be taken into account in the sensor detecting the diffusely reflected light by calculation. However, such an arrangement increases a data processing load.

Ideally, the reflecting plate for calibration should be disposed on the surface of the toner image bearing member, such as the photoreceptor and the intermediate transfer member to be detected because the surface of the toner image bearing member is a surface to be detected. However, disposing the reflecting plate on the surface of the toner image bearing member may disrupt image formation. Therefore, a method for disposing the reflecting plate for calibration on the sensor unit side is known.

For example, according to the Unexamined Utility Model Application Publication Hei 02-111162 described above, the shutter is provided to the detection surface side of the optical detection element (the toner adhesion sensor), and the calibration plate is disposed on the back of the shutter. Upon closing the shutter, the calibration plate may perform the sensitivity calibration.

However, because the calibration plate is disposed on the back of the shutter which is a moving member, positional reproducibility of the calibration plate may be poor due to the open-close movement of the calibration plate.

The output of the sensor is very sensitive to the distance to the object to detect. Thus, it is not preferable to dispose the calibration plate on the back of a device which moves repeatedly and has poor positional reproducibility.

According to Japanese Patent No. 3661446, the reference reflection surface (the equivalent of the reflecting plate for calibration) is disposed in the sensor (not the shutter), and fixed optical paths for calibration are provided between the reference reflection surface and the light emitting element, and between the reference reflection surface and the light receiving element, respectively.

According to this configuration, while normal detection is performed, the reflected light from the reference reflection surface enters the light receiving element through the fixed optical path for calibration, and the effect of the light passing through the fixed optical path for calibration is subtracted upon normal detection.

However, there may be a drawback to the foregoing configuration in that the output for calibration may be superimposed on the output for detection, thus shrinking the dynamic range detection output. Furthermore, every time normal detection is performed extra calculations need to be performed, thereby increasing the data processing load.

In view of the above, when normal detection is performed, it is desirable that the output value for calibration obtained from the reflected light from the reference reflection surface is not superimposed.

Another known arrangement is disclosed in Japanese Patent Laid-Open Application Publication 2002-268314, in which the reference reflection plate is provided in the vicinity of the light emitting element for the diffuse reflection in the optical sensor including two light emitting elements and a single light receiving element. A first optical path through which the reflected light from the measurement point enters the light receiving element, and a second optical path through which the reflected light by the reference reflection plate enters the light receiving element are also provided. An optical path intercepting member which intercepts either the first or the second optical path and opens the other path is provided.

The optical path intercepting member is driven by a solenoid disposed in the sensor housing. Although not explicitly indicated in Japanese Patent Laid-Open Application Publication 2002-268314, a contamination prevention shutter disposed in front of the sensor is driven to open and close by the solenoid in the sensor. As described above, when the driving force of the single solenoid is provided to the optical path intercepting member in the optical sensor and the shutter disposed outside the shutter, it is cost-effective. However, installation space for the solenoid and a mechanism to transmit its driving force requires space, increasing the size of the sensor unit.

SUMMARY OF THE INVENTION

In view of the foregoing, exemplary embodiments of the present invention provide an optical sensor capable of maintaining a stable output value for calibration so that the reliability of sensitivity calibration may be enhanced.

In one exemplary embodiment, an optical sensor for detecting image information includes a light-emitting element configured to direct light to an image, a light-receiving element configured to receive light reflected from the image, a normal detection optical path, a calibration reflecting plate, a calibration optical path, and a first optical function element. The normal detection optical path is configured to allow the light emitted by the light-emitting element and the light reflected from the image to follow a normal detection optical path during normal operation. The calibration reflecting plate is disposed inside the optical sensor and configured to reflect light from the light-emitting element when sensitivity is calibrated. The calibration optical path is configured to allow the light emitted by the light-emitting element to follow a calibration optical path to the light-receiving element that is different from the normal optical path when the emitted light is reflected by the calibration reflecting plate. The first optical function element is disposed in the calibration optical path and configured to be switchable between a light permeating state, in which the light passes therethrough, and a light intercepting state, in which the light is blocked, when voltage is applied.

Another exemplary embodiment provides an image forming apparatus including an image bearing member, an image forming unit, and the optical sensor described above. The image bearing member is configured to bear a toner image. The image forming unit is configured to form the toner image on the image bearing member. The optical sensor includes a light-emitting element, a light-receiving element, a normal detection optical path, a calibration reflecting plate, a calibration optical path, and a first optical function element.

Additional features and advantages of the present invention will be more fully apparent from the following detailed description of exemplary embodiments, the accompanying drawings and the associated claims.

BRIEF DESCRIPTION OF THE DRAWINGS

A more complete appreciation of the disclosure and many of the attendant advantages thereof will be readily obtained as the same becomes better understood by reference to the following detailed description of exemplary embodiments when considered in connection with the accompanying drawings, wherein.

DETAILED DESCRIPTION OF EXEMPLARY EMBODIMENTS

In describing exemplary embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner and achieve a similar result.

Exemplary embodiments of the present invention are now described below with reference to the accompanying drawings.

In a later described comparative example, exemplary embodiment, and alternative example, for the sake of simplicity of drawings and descriptions, the same reference numerals will be given to constituent elements such as parts and materials having the same functions, and redundant descriptions thereof will be omitted unless otherwise stated.

Typically, but not necessarily, paper is the medium from which is made a sheet on which an image is to be formed. It should be noted, however, that other printable media are available in sheet, and accordingly their use here is included. Thus, solely for simplicity, although this Detailed Description section refers to paper, sheets thereof, paper feeder, etc., it should be understood that the sheets, etc., are not limited only to paper, but includes other printable media as well.

Figure 1A:
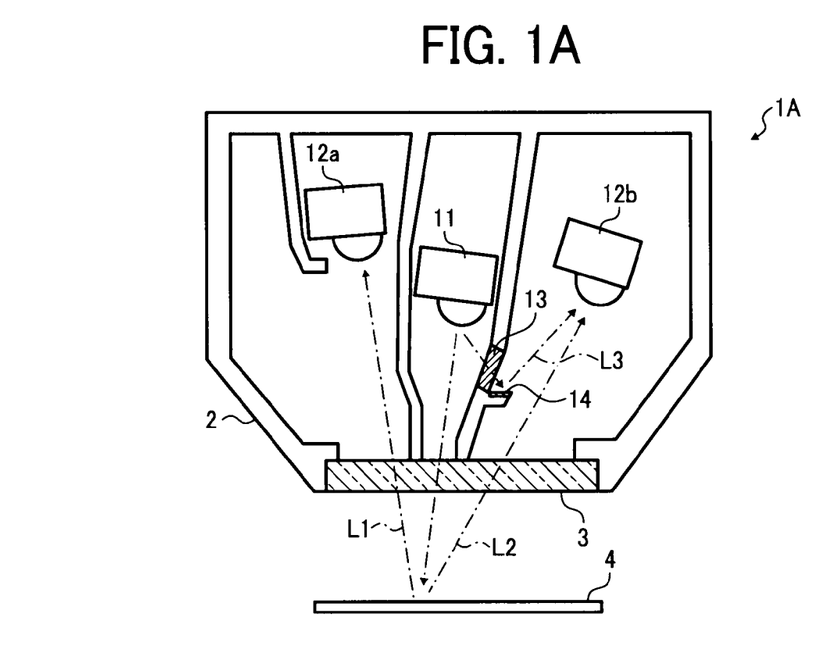
FIGS. 1A and 1B are cross-sectional views illustrating an optical sensor according to an exemplary embodiment of the present invention.
Figure 1B:
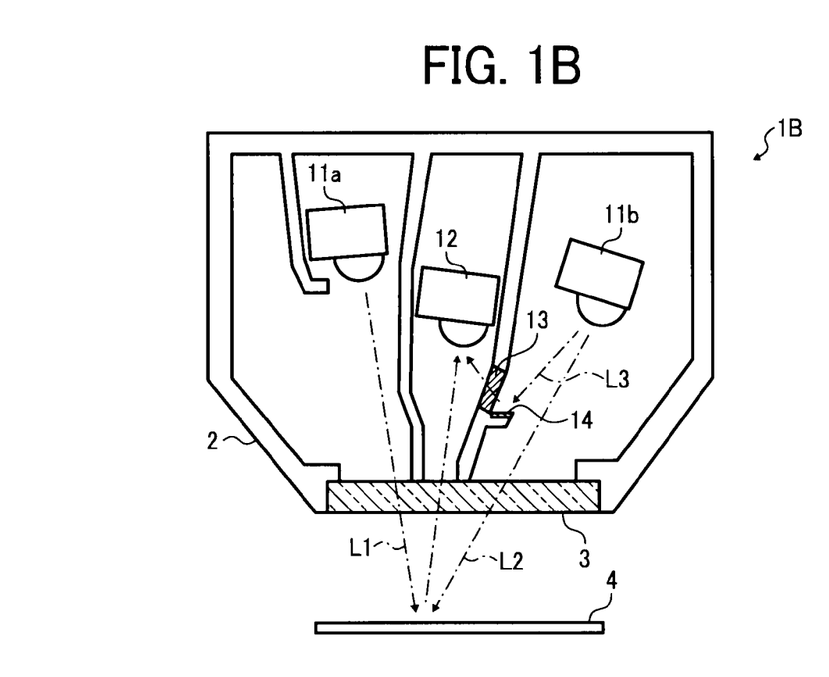

Referring now to the drawings, wherein like reference numerals designate identical or corresponding parts throughout the several views, and initially to FIGS. 1A and 1B, one example of an optical sensor according to an exemplary embodiment of the present invention is described.

Exemplary Embodiment 1

FIGS. 1A and 1B are cross-sectional views illustrating an optical sensor according to one exemplary embodiment of the present invention. The optical sensor illustrated in FIGS. 1A and 1B includes an optical function element disposed in a calibration optical path, switchable between a light permeating state, in which light is allowed to pass through, and a light intercepting state, in which light is blocked, when voltage is applied. In an image forming apparatus using dry toner, the optical sensor for detecting image information, particularly a color image forming apparatus, is most likely configured to detect both the specularly reflected light and the diffusely reflected light.

An optical sensor 1A illustrated in FIG. 1A includes at least one light emitting element 11 (normally, a light emitting diode (LED)) and two light receiving elements 12a and 12b (photodiodes or phototransistors), disposed within a sensor housing 2. The optical sensor 1A also includes a dust-proof glass or lens 3.

The light emitting element 11 is disposed such that the light emitting element 11 is tilted at a predetermined angle relative to a reflective surface 4 (such as a surface of an image bearing member, i.e., a photoreceptor or an intermediate transfer belt). The light receiving element 12a is disposed where the specularly reflected light enters relative to the light emitting element 11. The light receiving element 12b for receiving diffusely reflected light is disposed at an arbitrary position opposite the light receiving element 12a relative to the light emitting element 11.

The first exemplary embodiment is not limited to the structure described above, and alternatively, as illustrated in FIG. 1B, a reverse structure relative to the structure of FIG. 1A may be implemented. Thus, as illustrated in FIG. 1B, an optical sensor 1B includes at least one light receiving element 12, and two light emitting elements 11a and 11b in the sensor housing 2.

In the optical sensor 1B illustrated in FIG. 1B, the light receiving element 12 is disposed where the light emitting element 11 is disposed in FIG. 1A. The light emitting element 11a on the specular reflection side in FIG. 1B is disposed where the light receiving element 12a on the specular reflection side is disposed in FIG. 1A. The light emitting element 11b on the diffuse reflection side in FIG. 1B is disposed where the light receiving element 12b is disposed in FIG. 1A.

In FIG. 1B, arrows for indicating an optical path L1 for normal detection on the specular reflection side, an optical path L2 for normal detection on the diffuse reflection side, and an optical path L3 for calibration are reversed in FIG. 1A. Functions are similar, if not the same, between the structure of FIG. 1A and the structure of FIG. 1B. According to the exemplary embodiment, either structure can be applied.

As shown in FIGS. 1A and 1B, the optical sensor 1A (or 1B) includes a reflecting plate 14 for calibration (hereinafter referred to as a calibration reflecting plate 14). The calibration reflecting plate 14 is attached to one side of a wall separating the light emitting element 11 (or the light receiving element 12 of FIG. 1B) and the light receiving element 12b (or light emitting element 11b of FIG. 1B).

A portion of the wall includes an optical function element 13 switchable between a light permeating state, allowing the light to pass through, and a light intercepting state, in which the light is blocked by application of voltage. When supplied with voltage, the optical function element 13 is in the light permeating state, allowing the light to pass through, and the optical path L3 for calibration is formed. The optical function element 13 may be formed of a liquid crystal element, for example.

An optimum installation position of the calibration reflecting plate 14 relative to the light receiving element and the light emitting element depends on directional characteristics of the light emitting element 11 and the light receiving element 12b on the diffuse reflection side of FIG. 1A (or the light receiving element 12 and the light emitting element 11b on the diffuse reflection side of FIG. 1B). Thus, it is necessary to dispose the calibration reflecting plate 14 where the directional characteristics of both elements overlap.

Normally, the peak of the directional characteristics of both the light emitting element and the light receiving element is 0 degree (front). As the angle increases, the output or the sensitivity of the light emitting element and the light receiving element attenuates. Therefore, the reflecting plate 14 is disposed at a shallow angle relative to both elements, and it is desirable that the sensor is configured to accommodate such an installation position of the calibration reflecting plate 14.

In a case in which the calibration reflecting plate 14 cannot be disposed at a shallow angle relative to both elements, elements that have relatively broad directional characteristics (having a moderate attenuation ratio when the angle is increased) may need to be used.

Upon normal detection, light is blocked by the optical function element 13, and thus the light cannot pass through the optical path L3. Accordingly, the calibration reflecting plate 14 disposed in a manner described above does not reflect light.

When calibration is performed, the optical function element 13 is switched to the light permeating state, that is, a state that allows the light to pass through the optical function element 13, so that the optical path L3 is formed. As a result, a part of the light emitted by the light emitting element 11 of FIG. 1A (the light emitting element 11*b* of FIG. 1B on the diffuse reflection side) enters the calibration reflecting plate 14, and a part of the light reflected by the calibration reflecting plate 14 enters the light receiving element 12*b* of FIG. 1A of the diffuse reflection side (the light receiving element 12 of FIG. 1B).

As described above, by switching the state of the optical function element 13 from the light intercepting state in which the light is blocked to the light permeating state, the optical path L3 for calibration is formed, thereby making it possible to calibrate the sensitivity of the sensor on the diffuse reflection side consisting of the light emitting element 11 and the light receiving element 12*b* of FIG. 1A (the light emitting element 11*b* and the light receiving element 12 of FIG. 1B) using the calibration reflecting plate 14.

Exemplary Embodiment 2

Figure 2:
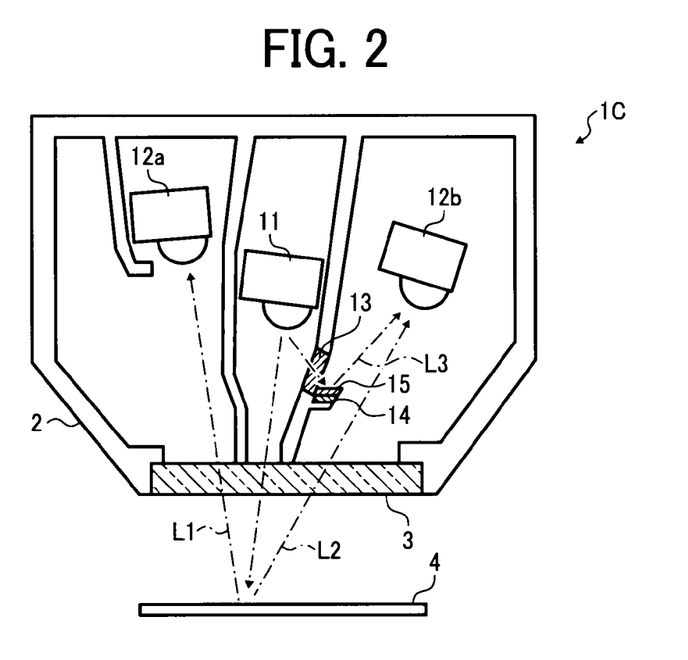
FIG. 2 is a cross-sectional view illustrating an optical sensor according to another exemplary embodiment of the present invention.

Referring now to FIG. 2, there is provided a cross-sectional view illustrating another exemplary embodiment of the present invention. FIG. 2 illustrates a second example of an optical sensor including an optical function element 15 disposed in front of the calibration reflecting plate 14. The optical function element 15 is switchable between the light permeating state and the light intercepting state when voltage is applied.

The structure of an optical sensor 1C in FIG. 2 is similar if not identical to, that of the optical sensor 1A illustrated in FIG. 1A. However, according to the second exemplary embodiment, the second optical function element 15 is provided in front of the calibration reflecting plate 14 illustrated in FIG. 1A. Similar to the optical function element 13 illustrated in FIG. 1A, the optical function element 15 may be formed of a liquid crystal element.

When calibration is performed in the optical sensor 1C, the state of both the optical function elements 13 and 15 is in the light permeating state, that is, a state in which light can pass through the optical function elements 13 and 15. Accordingly, the optical path L3 for calibration is formed, and the calibration reflecting plate 14 is put in an operable state. As a result, a portion of the light emitted by the light emitting element 11 is reflected by the calibration reflecting plate 14 and enters the light receiving element 12*b* on the diffuse reflection side, thereby making it possible to calibrate the light receiving element 12*b*.

When calibration is not performed, the optical function elements 13 and 15 are both in the light intercepting state, that is, the state in which the light is blocked. Accordingly, the optical path L3 is blocked, and the calibration reflecting plate 14 is in an inoperable state.

Upon normal detection, the light enters from the optical path L2 for normal detection on the diffuse reflection side. In such a case, it is assumed that the calibration reflecting plate 14 is disposed at a position causing no adverse effect. However, there is a possibility that there is an unintended light reflection in the sensor housing 2 and/or light leaking from the optical function element on the intercepting wall caused by deterioration of intercepting characteristics of the optical function element 13 and/or a gap between the elements caused by displacement of the elements, for example. In such cases, the light reflected by the calibration reflecting plate 14 enters the light receiving element 12*b* of the diffuse reflection side. Consequently, an error may be included in the output as normal detection is performed.

Accordingly, the optical function element 15 is disposed in front of the calibration reflecting plate 14 so as to shield the light immediately before the calibration reflecting plate 14, thereby reducing, if not preventing entirely, generation of light reflected by the calibration reflecting plate 14.

In a case in which the optical function element is formed of a liquid crystal element, the surface thereof may include a polarizing filter. In such a case, there is light reflected by the surface of the filter. Though light reflection may not be completely prevented, a significant amount of the light reflection component can be reduced, compared with the light reflection by the calibration reflecting plate 14. Therefore, errors caused by such disturbance can be reduced significantly.

Exemplary Embodiment 3

Figure 3:
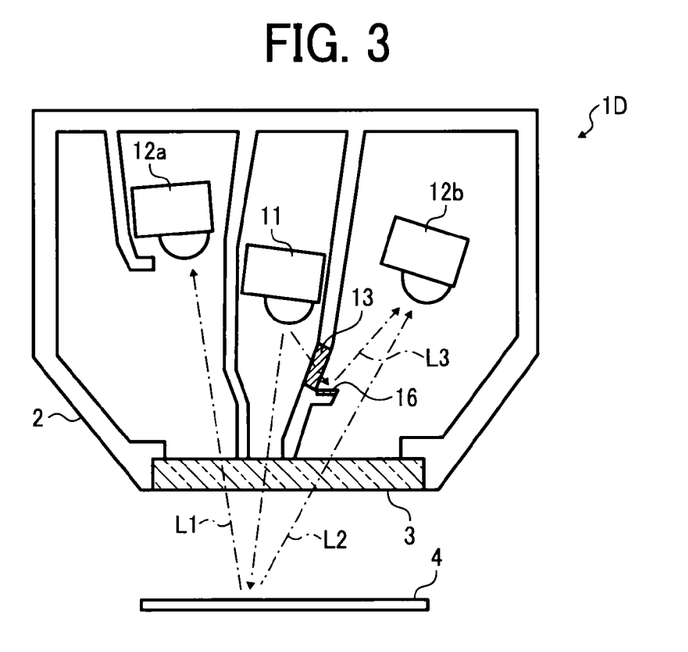
FIG. 3 is a cross-sectional view illustrating an optical sensor according to still another exemplary embodiment of the present invention.

Referring now to FIG. 3, there is provided a cross-sectional view illustrating still another exemplary embodiment of the present invention. FIG. 3 illustrates a third example of an optical sensor including an optical function element 16 serving as a reflecting plate for calibration. The optical function element 16 is switchable between the light permeating state and the light intercepting state when voltage is applied.

The structure of an optical sensor 1D is similar if not identical to, that of the optical sensor 1A illustrated in FIG. 1A. However, according to the exemplary embodiment, a white reference plate which is typical of a reflecting plate is not used. Instead, the optical function element 16 switchable between the light permeating state and the light intercepting state is provided. The optical function element 16 having such functions includes a light control mirror material developed by National Institute of Advanced Industrial and Technology, for example.

When calibration is performed in the optical sensor 1D illustrated in FIG. 3, the optical function element 13 on the wall is in the light permeating state, and the optical function element 16 serving as the reflecting plate for calibration is switched to the light reflecting state. Accordingly, the optical path L3 and the reflecting plate for calibration are formed, thereby enabling the optical function plate 16 serving as the reflecting plate for calibration to reflect the portion of the light emitted by the light emitting element 11. Subsequently, the reflected light enters the light receiving element 12*b*, thereby making it possible to calibrate the sensitivity of the light receiving element 12*b*.

When calibration is not performed, the optical function element 13 on the wall is switched to the light intercepting state, and the optical function element 16 is switched to the light permeating state. Accordingly, the optical path L3 is blocked, and the reflectivity of the reflecting plate for calibration is reduced. Thus, the incident light from the optical path L3 can be significantly reduced. Since there is a surface reflection, the reflectivity is not completely zero.

However, a significant amount of light is absorbed by the inner walls of the sensor housing 2, the color of which is black so as to reduce light reflection.

When there is unintended light reflection, for example, stray light and/or light leaking from the optical function element 13 on the wall, the light may be reflected if the reflecting plate for calibration is in the light reflecting state. Consequently, an error may occur in the output of the light receiving element 12*b*.

However, by switching the optical function element 16 to the light permeating state, the reflectivity of the optical function element 16 can be reduced, thereby making it possible to reduce error to a minimum.

When the optical function element 16 includes the light control mirror material, the surface of the light control mirror material is formed of glass material. Consequently, some surface reflection component may remain, even if the optical function element 16 is switched from a mirror state to the light permeating state. When compared with the reflection in the mirror state, however, the reflection component can be reduced so that the light reflection as a disturbance can be reduced significantly.

Exemplary Embodiment 4

Figure 4:
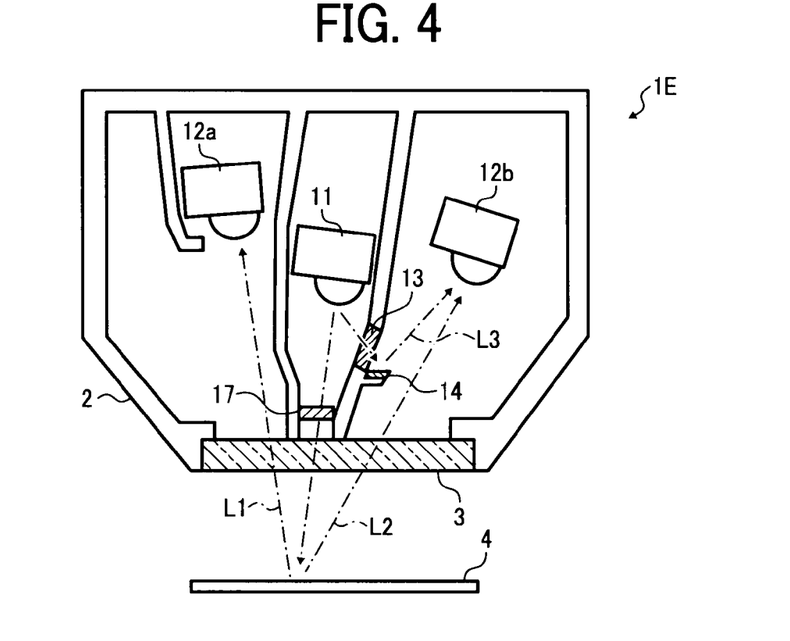
FIG. 4 is a cross-sectional view illustrating an optical sensor according to still another exemplary embodiment of the present invention.

Referring now to FIG. 4, there is provided a cross-sectional view illustrating still another exemplary embodiment of the present invention. FIG. 4 illustrates a fourth example of an optical sensor 1E that includes an optical function element 17 disposed in the optical path for normal detection, switchable between the light permeating state and the light intercepting state, when voltage is applied. During calibration, the optical function element 17 intercepts the optical path for normal detection.

The basic structure of the optical sensor 1E is similar if not identical to that of the optical sensor 1A illustrated in FIG. 1A. However, according to the exemplary embodiment, the optical function element 17 is disposed on a light projection path of the light emitting element 11 before the light is emitted from the optical sensor 1E. Notably, the optical function element 17 may be of a liquid crystal element which allows the light to pass through and be intercepted.

When calibration is performed, the optical function element 13 for the optical path L3 for calibration on the wall is switched to the light permeating state, and the optical function element 17 for the optical path for normal detection is switched to the light intercepting state. Accordingly, the light does not reach the optical path for normal detection outside the sensor. That is, there is no light entering the light receiving element 12b from the optical path for normal detection outside the sensor. In other words, only the light passing through the optical path L3 for calibration enters the light receiving element 12b, thereby reducing, if not prevented entirely, error caused by disturbance. Thus, highly reliable calibration can be performed.

The surface of the reflector in the image forming apparatus has a surface similar to the specular reflective surface. However, when the material of the reflector surface includes diffuse reflective components and/or is susceptible to a scratch or traces of friction that cause the surface of the reflector to have the diffuse reflective components, there is a possibility that the reflector surface may diffusely reflect light. In such a case, when calibration is performed, the diffusely reflected light may enter the light receiving element 12b passing through the optical path L2 for normal detection, causing error in the calibration.

However, when the optical function element 17 blocks the light from passing through the optical path for normal detection, causes of the error can be eliminated.

Furthermore, when normal detection is performed, the optical function element 13 is switched to the light intercepting state, and the optical function element 17 is switched to the light permeating state. Accordingly, the light can pass through only the optical path L1 and the optical path L2 for normal detection, thereby making it possible to effectively perform normal detection.

Figure 5:
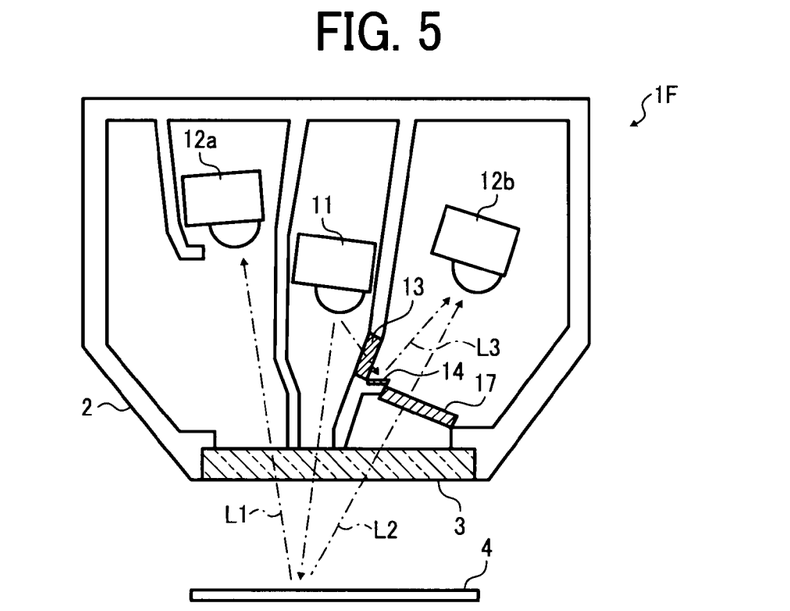
FIG. 5 is a cross-sectional view illustrating an optical sensor according to still another exemplary embodiment of the present invention.

Referring now to FIG. 5, there is provided an alternative example of the optical sensor of the fourth exemplary embodiment. Specifically, in FIG. 5 the optical function element 17 for the optical path for normal detection is disposed in the optical path L2 for normal detection on the diffuse reflection side.

According to this configuration, the light emitted from the light emitting element 11 is emitted outside the sensor and irradiates the reflector surface 4. Subsequently, the light diffusely reflected due to the reasons described above is intercepted by the optical function element 17 disposed in the optical path L2 on the diffuse reflection side. When calibration is performed, the optical function element 13 is switched to the light permeating state and the optical function element 17 is switched to the light intercepting state so that there is no incidence of light from the optical path L2, thus enabling calibration to be performed without error caused by a disturbance.

During calibration, the specular light can enter the light receiving element 12a for the specular reflection side as usual. Thus, it is advantageous that the detection function on the specular reflection side is operable, and detection on the specular reflection side can be performed in parallel with calibration of the light receiving element 12b.

Furthermore, similar to the embodiment illustrated in FIG. 4, when normal detection is performed, the optical function element 13 is switched to the light intercepting state, and the optical function element 17 is switched to the light permeating state, thereby making it possible to perform normal detection.

Exemplary Embodiment 5

Figure 6:
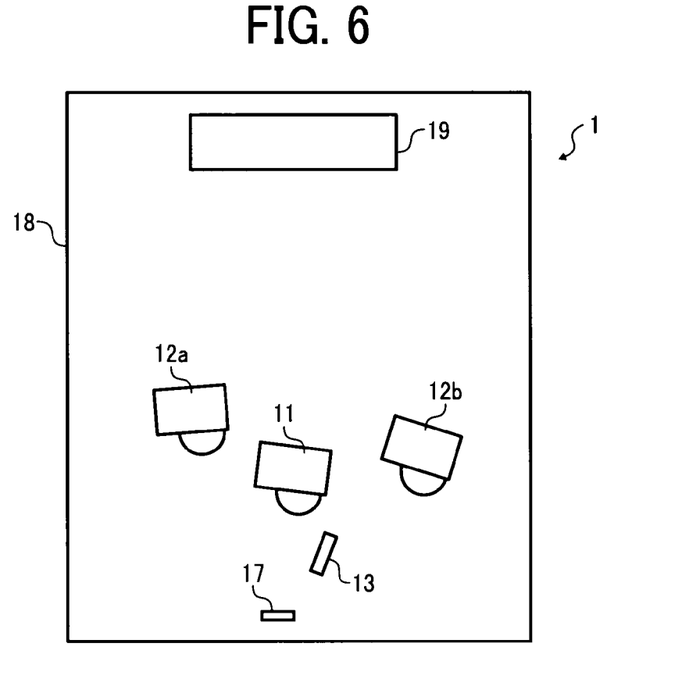
FIG. 6 is a schematic diagram illustrating a sensor substrate including components constituting the optical sensor of the exemplary embodiments.

Referring now to FIG. 6, there is provided a schematic diagram illustrating an exemplary structure of a sensor substrate 18 including electronic components constituting the optical sensor 1 of the exemplary embodiments described above. The electronic components include, for example, the light emitting element 11, the light receiving elements 12a and 12b, the optical function elements 13 and 17, a connector 19, and elements or the like that constitute a power supply circuit and an amplifier circuit.

FIG. 6 illustrates one example of the sensor substrate 18 based on allocation of the elements in the optical sensor 1E illustrated in FIG. 4. Although not illustrated, the sensor housing 2 of FIG. 4 covers substantially a bottom half of the sensor substrate 18. The sensor housing 2 may be configured to cover the entire sensor substrate 18. However, the structure of the sensor housing 2 illustrated in FIGS. 1 through 5 is configured to cover the substantially bottom half of the sensor substrate 18.

An example of the components disposed on the sensor housing 2, not on the sensor substrate 18, includes the calibration reflecting plate 14. As illustrated in FIGS. 1 through 5, the dust-proof glass or lens 3 may be fitted to the sensor housing 2.

The optical elements disposed on the sensor substrate 18 include the light emitting element 11, the light receiving elements 12a and 12b, the optical function elements 13 and 17, and so forth. The light emitting element 11 and the light receiving elements 12a and 12b are either a surface-mounted type or a discreet type in which the legs of the light emitting element and the light receiving elements are bent at 90 degrees and bonded to the sensor substrate 18 using solder.

The optical function elements are also bonded to the sensor substrate 18 using solder. It is to be noted that the fixing method is not limited to soldering, and accordingly, when soldering does not provide substantial fixing strength, any other suitable fixing method in addition to soldering can be applied, and the power can be supplied to electrodes through soldering.

The electronic components disposed in the above described manner are covered with the sensor housing 2. The position of the sensor housing 2 with respect to the sensor substrate 18 is determined by an alignment member, not shown, to form the optical sensor 1 covered with the sensor housing 2.

When the optical elements are disposed on the sensor substrate in the above-described manner, each optical element can be driven at a predetermined timing, enabling the optical sensor to operate as described above. It should be noted that FIGS. 1 through 5 illustrate a structure of a head portion of the optical sensor covered by the sensor housing 2.

Exemplary Embodiment 6

Figure 7:
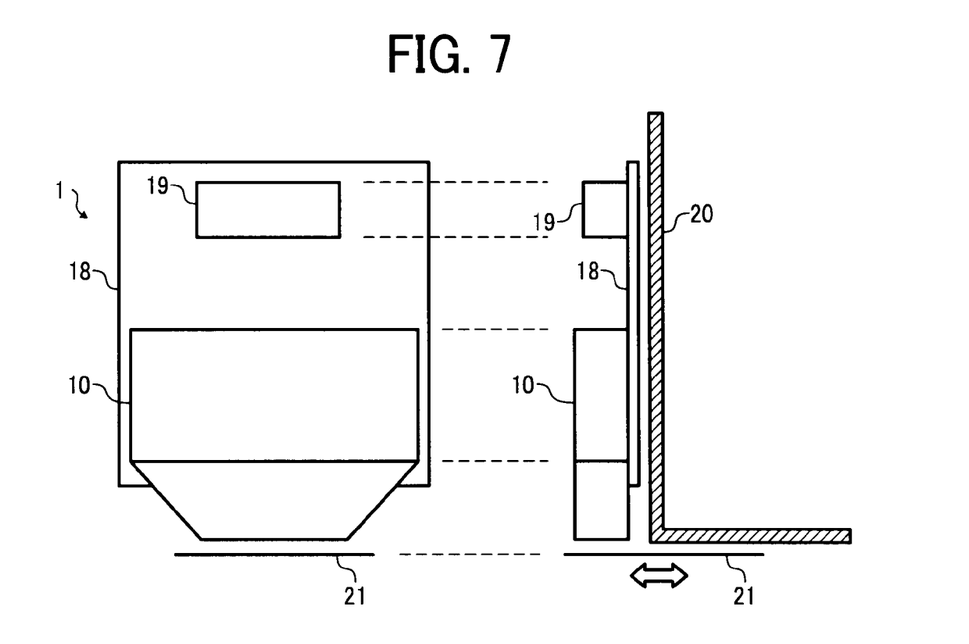
FIG. 7 is a conceptual diagram illustrating an optical sensor according to still another exemplary embodiment of the present invention.

Referring now to FIG. 7, there is provided a conceptual diagram illustrating an optical sensor according to still another exemplary embodiment of the present invention. FIG. 7 illustrates corresponding front and side views of the optical sensor 1 including a shutter member 21 for preventing a detection surface of a sensor head 10 of the optical sensor 1 from getting contaminated.

Normally, the shutter member 21 is fixed to a sensor bracket 20 on which the sensor substrate 18 is movably mounted. The shutter member 21 is driven to move reciprocally back and forth between a closing position and an opening position of the optical path for normal detection of the optical sensor by the driving force of a not-shown driving member such as a solenoid and a motor on the sensor bracket 20.

In FIG. 7, a double-headed arrow indicates the moving direction of the shutter member 21. However, the moving direction is not limited to a linear direction shown by the arrow, and alternatively the shutter member 21 may move back and forth in an arc.

In the optical sensor 1 in which the shutter member 21 is disposed in the manner described above, when the optical sensor head 10 has a structure similar to, if not the same as, that of the optical sensor 1A as illustrated in FIG. 1A, for example, calibration can be performed in conjunction with the movement of the shutter member 21 in such a manner that, when the shutter member 21 is closed, the optical function element 13 (for the calibration optical path) of FIG. 1A is switched to the light permeating state, and when the shutter member 21 is opened, the optical function element 13 is switched to the light intercepting state.

When the shutter member 21 is closed, the optical paths L1 and L2 are blocked. Thus, stable calibration can be performed by switching only the optical function element 13 to the light permeating state to open the optical path L3 for calibration. When the shutter member 21 is opened, there is a possibility that normal detection may be performed. Thus, the optical function element 13 is configured to block the optical path L3 so that the output for calibration is not superimposed on the output of normal detection.

As described above, when the shutter member 21 is provided, it is not necessary to provide the optical function element 17 dedicated to blocking the optical path for normal detection. It should be noted that a similar if not identical effect can be achieved when the shutter member 21 is implemented in the structures shown in FIGS. 1B, 2, and 3.

Exemplary Embodiment 7

Figure 8:
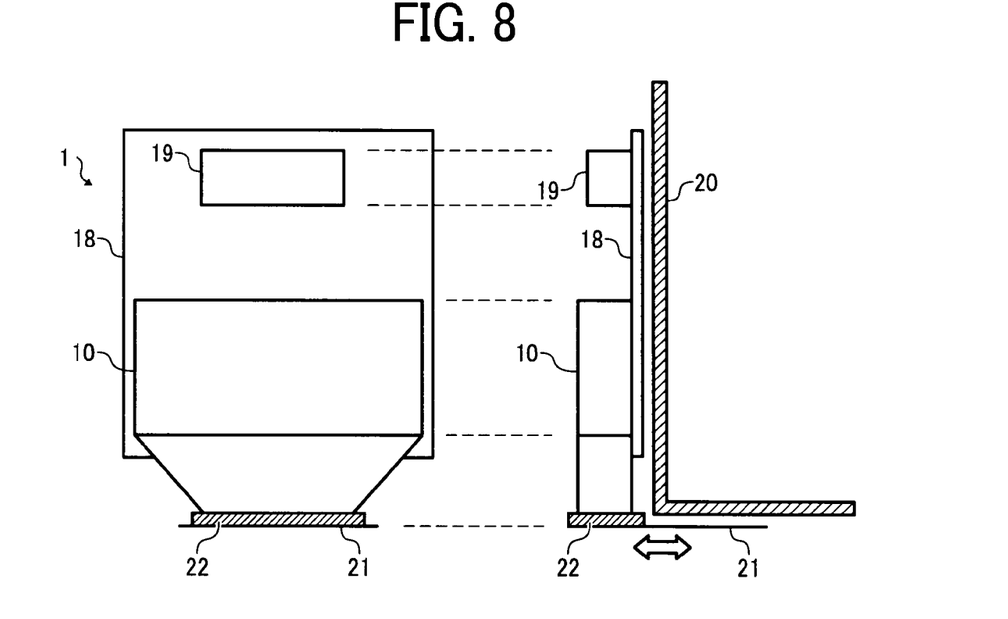
FIG. 8 is a conceptual diagram illustrating an optical sensor, according to still another exemplary embodiment of the present invention.

Referring now to FIG. 8, there is provided a conceptual diagram illustrating an optical sensor according to still another exemplary embodiment of the present invention. FIG. 8 illustrates corresponding front and side views of the optical sensor 1, including a cleaning member 22 provided to a surface of the shutter member 21 facing the optical sensor head 10. The optical sensor 1 has a similar if not the same structure as that of the optical sensor illustrated in FIG. 7.

As illustrated in FIG. 8, when the shutter member 21 is closed, the cleaning member 22 comes into contact with the dust-proof glass or lens 3 of the optical sensor head 10 from which light enters and exits. Accordingly, the optical path outside the optical sensor is intercepted.

It should be noted that the structure of the optical sensor 1 (the optical sensor head 10, the sensor substrate 18, and the connector 19), the sensor housing 20, and the shutter member 21 is similar to, if not the same as, that of FIG. 7, the difference being that the cleaning member 22 is disposed on the back of the shutter member 21.

The cleaning member 22 may be made of a material such as felt or the like. According to the exemplary embodiment, such a cleaning member is disposed on the back of the shutter member and comes into contact with the dust-proof glass or lens 3 of the optical sensor head 10 as illustrated in FIGS. 1 through 3, for example.

Accordingly, when the shutter member 21 is opened or closed, the cleaning member 22 moves back and forth wiping the surface of the dust-proof glass (or lens) 3 of the optical sensor head 10. When the shutter member 21 is in its closed position and stopped, the cleaning member 22 is in contact with the dust-proof glass (or lens) 3, thereby blocking the optical paths L1 and L2. The reflected light does not enter the optical path L2 for normal detection of the diffuse reflection.

Thus, as described above, by disposing the cleaning member 22 on the back of the shutter member 21 so as to abut the dust-proof glass (or lens) 3, it is not necessary to dispose the optical function element 17 that opens and blocks the optical path for normal detection.

Exemplary Embodiment 8

Figure 9:
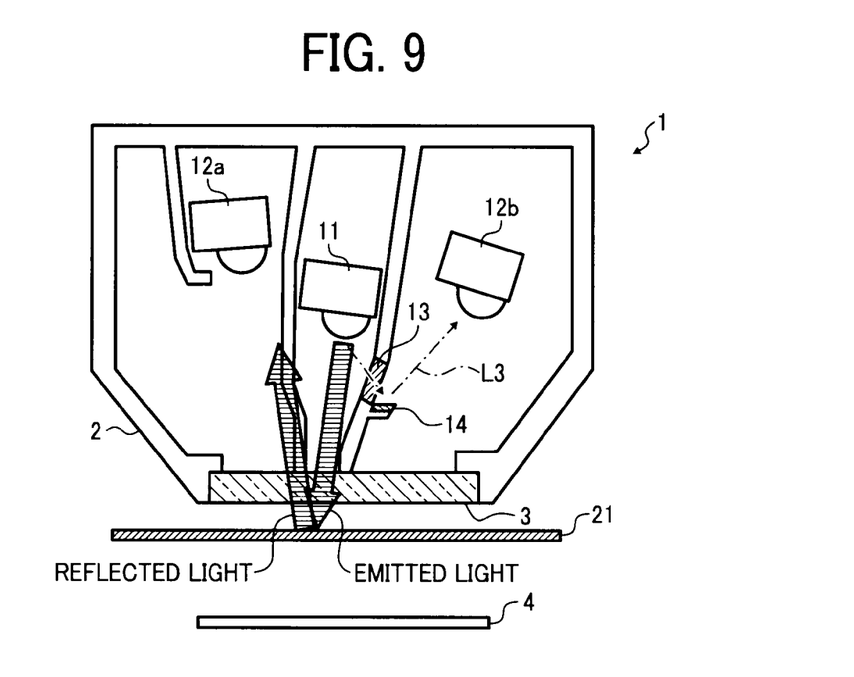
FIG. 9 is a cross-sectional view illustrating an optical sensor according to still another exemplary embodiment of the present invention.

Referring now to FIG. 9, there is provided a cross-sectional view illustrating an optical sensor when the surface of the shutter member 21 facing the optical sensor head has a specular reflective surface, according to still another exemplary embodiment of the present invention.

FIG. 9 illustrates paths of the light emitted from the light emitting element 11 and reflected by the shutter member 21. In FIG. 9, the shutter member 21 illustrated in FIG. 7 is provided between the dust-proof glass (or lens) 3 and the reflector surface 4.

According to the exemplary embodiment illustrated in FIG. 7, the optical path for normal detection is blocked by the shutter member 21. Thus, in principle, no light enters the light receiving element 12b on the diffuse reflection side from the optical path for normal detection. However, depending on the condition of a rear surface of the shutter member 21, there may be some slight incidence of light.

For example, when the rear surface which is a surface facing the reflector surface 4 has a diffusely reflective surface, the emitted light illustrated in FIG. 9 irradiates the rear surface of the shutter member 21, generating the diffusely reflected light. Among the diffusely reflected light, there may be a component that is reflected back to the light receiving element 12b on the diffuse reflection side.

In view of the above, according to the exemplary embodiment, the rear surface of the shutter member 21 has the specular reflective surface so that the light is specularly reflected, generating the specular light and preventing the light from being reflected back to the diffuse reflection side. Accordingly, when the shutter member 21 is closed, the incidence of light from the optical path for normal detection on the diffuse reflection side is reduced, if not prevented entirely, making it possible to perform highly reliable calibration.

It should be noted that, when performing calibration, the optical function element 13 in FIG. 9 is in the light permeating state, allowing the light to enter the light receiving element 12b through the optical path L3 for calibration indicated by a dotted line. Accordingly, calibration of the light receiving element 12b can be performed by the light entering the light receiving element 12b.

Exemplary Embodiment 9

Figure 10:
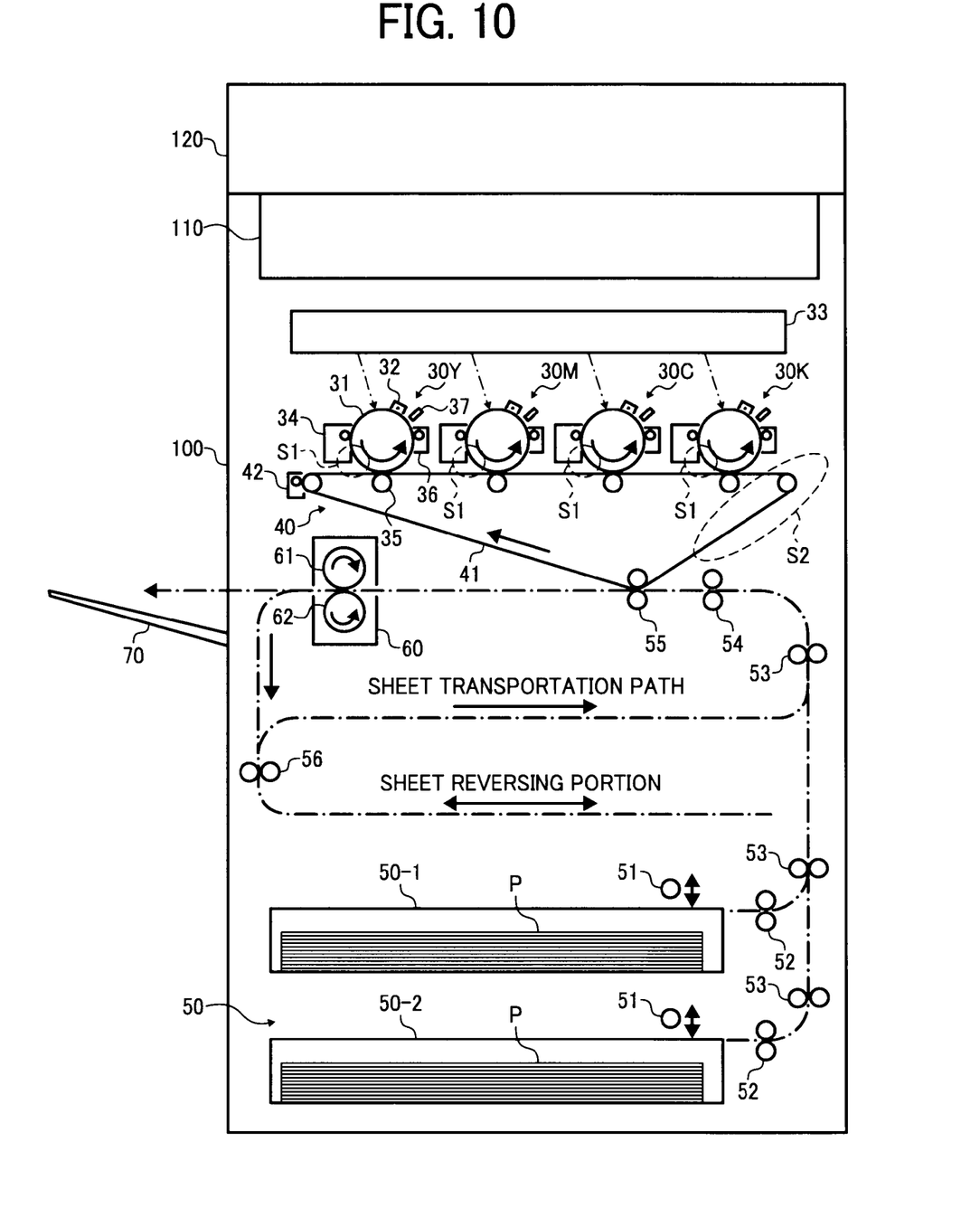
FIG. 10 is a schematic diagram illustrating an image forming apparatus, according to an exemplary embodiment of the present invention.

Referring now to FIG. 10, there is provided a schematic diagram illustrating an image forming apparatus including an optical sensor according to the exemplary embodiments 1 through 8.

The image forming apparatus according to the exemplary embodiment may be a four-tandem-type full-color image forming apparatus using an intermediate transfer method, such as a copier, printer, a facsimile, and a multi-function machine including the functions of the copier, the printer, and the facsimile. It is to be noted that the image forming apparatus is not limited to the four-tandem type using the intermediate transfer method, and therefore the image forming apparatus may be a four-tandem-type using a direct transfer method or a single-drum type full-color image forming apparatus using the intermediate transfer method.

There is no reason to install the optical sensor of the present invention in the monochrome image forming apparatus. Normally, adhesion of monochrome toner, that is, black toner, is detected using the specular reflection method, not the diffuse reflection method. Therefore, the optical sensor of the present invention is applicable to a full-color image forming apparatus.

An image forming apparatus 100 illustrated in FIG. 10 includes at least, in substantially the center thereof, a printer unit serving as an image forming unit of the four-tandem-type image forming apparatus using the intermediate transfer method. A scanner 110 serving as an image reading unit for reading a document image is disposed at an upper portion of the image forming apparatus 100. Above the scanner 110 is provided an automatic document feeder (ADF) 120, which automatically feeds a document to a contact glass, not shown, of the scanner 110. At a bottom of the image forming apparatus 100 is provided a sheet feed unit 50 including sheet feed cassettes 50-1 and 50-2, each storing a sheet-type recording medium of a standard size, for example.

In the four-tandem-type printer unit using the intermediate transfer method, four image forming units 30Y for yellow, 30M for magenta, 30C for cyan, and 30K for black are aligned along an intermediate transfer belt 41 of a transfer mechanism 40. The intermediate transfer belt 41 is an intermediate transfer member serving as an image bearing member after primary transfer.

The structure of each of four image forming units 30Y, 30M, 30C and 30K is similar if not identical. Each of the image forming units 30Y, 30M, 30C, and 30K includes a photoreceptor 31 serving as an image bearing member. Surrounding each photoreceptor 31 are at least: A charging unit 32 such as a charger, a charging roller, a charging brush, and the like; a developing unit 34; a primary transfer unit 35 such as a primary transfer roller, a primary transfer charger, and the like; a photoreceptor cleaning unit 36 such as a cleaning blade, a cleaning brush, and the like; and a charge neutralization device 37 such as a charge neutralization lamp, a charge discharger, and the like. A writing unit 33, such as an optical writing unit of a laser scanning type or a line-shape optical writing unit using an LED array and an imaging element array, is disposed substantially above the four image forming units 30Y, 30M, 30C, and 30K.

In each of the image forming units 30Y, 30M, 30C, and 30K, the charging unit 32 charges the photoreceptor 31. The writing unit 33 emits light and irradiates the photoreceptor surface according to image information to form an electrostatic latent image on the photoreceptor surface. The image information includes image information of a document which has been scanned by the scanner 110, image information input by an external personal computer or the like, or image information received from a communication line, or the like.

The electrostatic latent image on each photoreceptor is developed with toner of a respective color, thereby forming images in different developing colors or toner colors. For example, toner images of yellow (Y), magenta (M), cyan (C), and black (BK) are sequentially formed from the left in FIG. 10. Subsequently, the toner images of different colors, with one color image on each photoreceptor, are sequentially and overlappingly transferred (called primary transfer) onto the intermediate transfer belt 41 by the primary transfer unit 35, thereby forming a full-color image.

After the primary transfer process, the photoreceptor 31 is cleaned by the photoreceptor cleaning unit 36 to remove any toner remaining on the surface of the photoreceptor 31. Subsequently, the charge neutralization device 37 removes any residual charge from the photoreceptor 31.

The transfer mechanism 40 includes at least the intermediate transfer belt 41 spanned between a plurality of rollers including a drive roller and a driven roller; the primary transfer unit 35; a belt cleaning unit 42 such as a cleaning blade, a cleaning brush, and the like; and a secondary transfer unit 55 including a secondary transfer roller, a secondary transfer charger, and the like.

The color image overlappingly transferred from each of the photoreceptors 31 of the image forming units 30Y, 30M, 30C, and 30K to the intermediate transfer belt 41 is transported by the transfer mechanism 40 to a secondary transfer portion at which a secondary transfer unit 55 is disposed.

In the sheet feeding unit 50, the recording sheet P stored in the sheet feed cassette 50-1 or 50-2 is fed by a pick-up roller 51 and a sheet feed roller 52, and transported to a registration roller 54 by a conveyance roller 53.

The registration roller 54 feeds the recording sheet P to the secondary transfer portion at an appropriate time, such that the image transported by the intermediate transfer belt 41 is aligned with the secondary transfer unit 55.

In the secondary transfer portion, the image is secondarily transferred onto the recording sheet P from the intermediate transfer belt 41 by the secondary transfer unit 55. Subsequently, the recording sheet P after the image is transferred thereon is separated from the intermediate transfer belt 41 and transported to a fixing unit 60. The toner remaining on the intermediate transfer belt 41 after the image is transferred is removed from the intermediate transfer belt 41 by the belt cleaning unit 42.

The image transferred onto the recording sheet P in the secondary transfer portion is heated and pressed by a heating roller 61 and a pressure roller 62 of the fixing unit 60 to fix the image onto the recording sheet P. The recording sheet P onto which the image is fixed is then ejected to a catch tray 70.

It should be noted that the heating roller 61 and the pressure roller 62 are not limited to a roller. Thus, for example, the heating roller 61 and the pressure roller 62 may be a belt.

It is possible to perform duplex printing in the image forming apparatus 100, in which the image can be formed on both sides of the recording sheet P. When performing duplex printing, the recording sheet P after passing the fixing unit 60 is transported to a sheet reversing portion so that the recording sheet P is turned upside down by a switch-back roller 56 and sent to a reverse sheet conveyance path. The recording sheet P is transported to the registration roller 54 again via the conveyance roller 53. Subsequently, the image is transferred onto the back of the recording sheet P in the secondary transfer portion, and fixed by the fixing unit 60. The recording sheet is then ejected onto the catch tray 70.

The foregoing description is of one example of the structure and the operation of the image forming apparatus according to the exemplary embodiment of the present invention. When the optical sensor 1 according to the exemplary embodiments is installed in the full-color image forming apparatus illustrated in FIG. 10, the optical sensor 1 can be disposed at sensor installation position S1 or sensor installation position S2 indicated by dotted circles.

The sensor installation positions S1 are each located across from the photoreceptor 31 in an area between the developing unit 34 and the primary transfer unit 35 of each of the image forming units 30Y, 30M, 30C, and 30K. According to this structure, the surface of the photoreceptor refers to the reflector surface 4 facing the above-described optical sensor 1 (1A through 1F).

The sensor installation position S2 is located across from the intermediate transfer belt 41 in an area before the image transferred onto the intermediate transfer belt 41 reaches the secondary transfer unit 55. According to this structure, the surface of the intermediate transfer belt 41 refers to the reflector surface 4 facing the above-described optical sensor 1 (1A through 1F).

The optical sensor 1 (1A through 1F) according to the exemplary embodiments serves as a sensor that measures the amount of toner adhesion. When the amount of toner adhering on the intermediate transfer belt 41 is measured, the installation position of the optical sensor 1 (1A through 1F) may be limited to the sensor installation position S2 of FIG. 10 where the toner images of four different colors are overlaid, but not yet transferred onto the recording sheet P.

Alternatively, the optical sensor 1 may be provided at each of the sensor installation positions S1 where the toner images of different colors are formed in the respective image forming units 30Y, 30M, 30C, and 30K for different colors. In such a case, basically, the optical sensor for the black toner is provided with the light receiving element and the light emitting element for the specular reflection. The optical sensor for the color toners is provided with the light receiving element and the light emitting element for the diffuse reflection.

However, if there is a problem in the detection or calibration operations when using either the specular reflection component or the diffuse reflection component, the light receiving element and the light emitting element for the specular reflection and the light receiving element and the light emitting element for the specular reflection for the diffuse reflection can be provided for each color.

As described above, when the optical sensor according to the exemplary embodiments is disposed in the image forming apparatus, the light receiving element for the diffuse reflection can be calibrated by using the reflection plate for calibration. As a result, stable control of the adherence of color toners can be achieved, thereby enhancing the image quality of the images provided by the image forming apparatus.

Furthermore, elements and/or features of different exemplary embodiments may be combined with each other and/or substituted for each other within the scope of this disclosure and appended claims.

The number of constituent elements, their locations, shapes and so forth of the constituent elements are not limited to any of the structure for performing the methodology illustrated in the drawings.

Example embodiments being thus described, it will be obvious that the same may be varied in many ways. Such exemplary variations are not to be regarded as a departure from the spirit and scope of the present invention, and all such modifications as would be obvious to one skilled in the art are intended to be included within the scope of the following claims.

What is claimed is:

1. An optical sensor for detecting image information, comprising:
    a light-emitting element configured to direct light to an image;
    a light-receiving element configured to receive light reflected from the image;
    a normal detection optical path configured to allow the light emitted by the light-emitting element and the light reflected from the image to follow a normal detection optical path during normal operation;
    a calibration reflecting plate disposed inside the optical sensor, configured to reflect light from the light-emitting element when sensitivity is calibrated;
    a calibration optical path from the light-emitting element to the light-receiving element that is different from the normal optical path utilized when the emitted light is reflected by the calibration reflecting plate; and
    a first optical function element disposed in the calibration optical path, configured to be switchable between a light permeating state, in which the light passes therethrough, and a light intercepting state, in which the light is blocked, when voltage is applied.

2. The optical sensor according to claim 1, further comprising a second optical function element disposed in front of the calibration reflecting plate, configured to be switchable between the light permeating state and the light intercepting state when voltage is applied.

3. The optical sensor according to claim 1, wherein the calibration reflecting plate is switchable between the light permeating state and a light reflecting state in which light is reflected.

4. The optical sensor according to claim 1, further comprising:
    a second optical function element disposed in the normal detection optical path, configured to be switchable between the light permeating state and the light intercepting state when voltage is applied,
    wherein during calibration the second optical function element blocks the normal detection optical path.

5. The optical sensor according to claim 1, further comprising a shutter disposed at a detection surface of the optical sensor, configured to prevent the detection surface from getting contaminated, wherein the first optical function element controls the calibration optical path such that, when the shutter is closed, calibration is performed, and when the shutter is opened, calibration is not performed.

6. The optical sensor according to claim 5, further comprising a cleaning member disposed on a surface of the shutter facing the optical sensor,
wherein when the shutter is closed, the cleaning member comes into contact with a surface of the optical sensor from which the light enters and exits to block a light path outside the sensor.

7. The optical sensor according to claim 5, wherein the surface of the shutter facing the optical sensor comprises a specular reflective surface.

8. An image forming apparatus, comprising at least:
an image bearing member configured to bear a toner image;
an image forming unit configured to form the toner image on the image bearing member; and
an optical sensor configured to detect image information, the optical sensor including:
a light-emitting element configured to direct light to an image;
a light-receiving element configured to receive light reflected by the image;
a normal detection optical path configured to allow the light emitted by the light-emitting element and the light reflected from the image to follow a normal detection optical path during normal operation;
a calibration reflecting plate disposed inside the optical sensor, configured to reflect light from the light-emitting element when sensitivity is calibrated;
a calibration optical path from the light-emitting element to the light-receiving element that is different from the normal optical path utilized when the emitted light is reflected by the calibration reflecting plate; and
a first optical function element disposed in the calibration optical path, configured to be switchable between a light permeating state, in which the light passes therethrough, and a light intercepting state, in which the light is blocked, when voltage is applied.

9. The image forming apparatus according to claim 8, wherein the optical sensor is disposed in the vicinity of the image bearing member and configured to measure an amount of toner adhering to the surface of the image bearing member by irradiating the toner image formed on the image bearing member surface and detecting an amount of a reflected light.

10. The image forming apparatus according to claim 9, wherein the image bearing member is a photoreceptor.

11. The image forming apparatus according to claim 9, wherein the image bearing member is an intermediate transfer member onto which the toner image formed on a photoreceptor is transferred.

* * * * *